(12) United States Patent
Bisegna et al.

(10) Patent No.: US 9,855,390 B2
(45) Date of Patent: *Jan. 2, 2018

(54) PLUNGER COVERS AND PLUNGERS FOR USE IN SYRINGES

(71) Applicant: BAYER HEALTHCARE LLC, Whippany, NJ (US)

(72) Inventors: Joseph E. Bisegna, Cheswick, PA (US); Jared E. Neff, New Kensington, PA (US)

(73) Assignee: BAYER HEALTHCARE LLC, Whippany, NJ (US)

( * ) Notice: Subject to any disclaimer, the term of this patent is extended or adjusted under 35 U.S.C. 154(b) by 92 days.

This patent is subject to a terminal disclaimer.

(21) Appl. No.: 14/576,354

(22) Filed: Dec. 19, 2014

(65) Prior Publication Data

US 2015/0105736 A1    Apr. 16, 2015

Related U.S. Application Data

(62) Division of application No. 11/686,000, filed on Mar. 14, 2007, now Pat. No. 8,926,569.

(60) Provisional application No. 60/782,623, filed on Mar. 15, 2006.

(51) Int. Cl.
*A61M 5/315* (2006.01)

(52) U.S. Cl.
CPC ............... *A61M 5/31513* (2013.01)

(58) Field of Classification Search
CPC .......... A61M 5/31515; A61M 5/31513; B29C 45/1676
See application file for complete search history.

(56) References Cited

U.S. PATENT DOCUMENTS

| 1,687,323 A | 10/1928 | Cook |
| 1,988,480 A | 1/1935 | Campkin |
| 2,392,196 A | 1/1946 | Smith |
| 2,419,401 A | 4/1947 | Hinds |

(Continued)

FOREIGN PATENT DOCUMENTS

| AU | 317487 | 4/2012 |
| DE | 2919978 A1 | 11/1980 |

(Continued)

OTHER PUBLICATIONS

The International Search Report and Written Opinion dated Feb. 23, 2015 from related PCT Application No. PCT/US2014/067435 filed on Nov. 25, 2014.

(Continued)

*Primary Examiner* — Bradley Osinski
(74) *Attorney, Agent, or Firm* — David Schramm; Joseph L. Kent; James R. Stevenson

(57) ABSTRACT

A plunger cover for use with a syringe includes a sealing portion adapted to form a seal with the syringe and a central portion adapted to contact fluid within the syringe. The central portion can, for example, be more rigid than the sealing portion. The sealing portion and the central portion are connected in an overmolding process. The sealing portion can, for example, be formed from a thermoplastic elastomer or a thermoplastic polyurethane. The central portion can, for example, be formed from polypropylene, acrylonitrile butadiene styrene, polycarbonate or copolymers thereof.

17 Claims, 10 Drawing Sheets

(56) References Cited

U.S. PATENT DOCUMENTS

| | | |
|---|---|---|
| 2,702,547 A | 2/1955 | Glass |
| 2,842,126 A | 7/1958 | Brown |
| 3,051,173 A | 8/1962 | Johnson et al. |
| D203,730 S | 2/1966 | Coanda |
| 3,270,483 A | 9/1966 | Smoyer et al. |
| 3,348,545 A | 10/1967 | Sarnoff et al. |
| 3,468,471 A | 9/1969 | Fritz |
| 3,604,417 A | 9/1971 | Sidney |
| 3,623,474 A | 11/1971 | Marlin et al. |
| 3,645,262 A | 2/1972 | Robert |
| 3,701,345 A | 10/1972 | Marlin et al. |
| 3,705,582 A | 12/1972 | Marvin et al. |
| 3,720,211 A | 3/1973 | Kyrias |
| 3,738,539 A | 6/1973 | Beich |
| 3,752,145 A | 8/1973 | Runnells et al. |
| 3,796,218 A | 3/1974 | Burke et al. |
| 3,812,843 A | 5/1974 | Wootten et al. |
| 3,902,491 A | 9/1975 | Lajus |
| 3,964,139 A | 6/1976 | Kleinmann et al. |
| 3,987,940 A | 10/1976 | Tischlinger |
| 3,998,224 A | 12/1976 | Chiquiar-Arias |
| 4,006,736 A | 2/1977 | Kranys et al. |
| 4,030,498 A | 6/1977 | Tompkins |
| 4,080,967 A | 3/1978 | O'Leary |
| 4,148,316 A | 4/1979 | Xanthopoulos |
| 4,155,490 A | 5/1979 | Glenn |
| 4,159,713 A | 7/1979 | Prais |
| 4,180,006 A | 12/1979 | Ross |
| 4,180,069 A | 12/1979 | Walters |
| 4,226,236 A | 10/1980 | Genese |
| 4,252,118 A | 2/1981 | Richard et al. |
| 4,278,086 A | 7/1981 | Hodgins et al. |
| 4,303,070 A | 12/1981 | Ichikawa et al. |
| 4,345,595 A | 8/1982 | Whitney et al. |
| 4,351,332 A | 9/1982 | Whitney et al. |
| 4,356,822 A | 11/1982 | Winstead-Hall |
| 4,424,720 A | 1/1984 | Bucchianeri |
| 4,452,251 A | 6/1984 | Heilman |
| 4,453,934 A | 6/1984 | Gaehwiler et al. |
| 4,464,265 A | 8/1984 | Joyner |
| 4,465,472 A | 8/1984 | Urbaniak |
| 4,465,473 A | 8/1984 | Rueegg |
| 4,475,666 A | 10/1984 | Bilbrey et al. |
| 4,476,381 A | 10/1984 | Rubin |
| 4,490,256 A | 12/1984 | Nussbaumer et al. |
| 4,493,646 A | 1/1985 | Lacour et al. |
| 4,500,310 A | 2/1985 | Christinger |
| 4,529,401 A | 7/1985 | Leslie et al. |
| 4,562,844 A | 1/1986 | Carpenter et al. |
| 4,568,335 A | 2/1986 | Updike et al. |
| 4,573,978 A | 3/1986 | Reilly |
| 4,585,439 A | 4/1986 | Michel |
| 4,604,847 A | 8/1986 | Moulding, Jr. et al. |
| 4,612,010 A | 9/1986 | Hamacher et al. |
| 4,617,016 A | 10/1986 | Blomberg |
| 4,628,969 A | 12/1986 | Jurgens, Jr. et al. |
| 4,636,198 A | 1/1987 | Stade |
| 4,648,872 A | 3/1987 | Kamen |
| 4,650,475 A | 3/1987 | Smith et al. |
| 4,652,260 A | 3/1987 | Fenton, Jr. et al. |
| 4,664,128 A | 5/1987 | Lee |
| 4,676,776 A | 6/1987 | Howson |
| 4,677,980 A | 7/1987 | Reilly et al. |
| 4,677,981 A | 7/1987 | Coursant |
| 4,681,566 A | 7/1987 | Fenton, Jr. et al. |
| 4,685,903 A | 8/1987 | Cable et al. |
| 4,695,271 A | 9/1987 | Goethel |
| 4,705,509 A | 11/1987 | Stade |
| 4,718,463 A | 1/1988 | Jurgens, Jr. et al. |
| 4,722,734 A | 2/1988 | Kolln |
| 4,741,732 A | 5/1988 | Crankshaw et al. |
| 4,741,736 A | 5/1988 | Brown |
| 4,749,109 A | 6/1988 | Kamen |
| 4,755,172 A | 7/1988 | Baldwin |
| 4,767,406 A | 8/1988 | Wadham et al. |
| 4,773,900 A | 9/1988 | Cochran |
| 4,838,857 A | 6/1989 | Strowe et al. |
| 4,840,616 A | 6/1989 | Banks |
| 4,842,581 A | 6/1989 | Davis |
| RE32,974 E | 7/1989 | Porat et al. |
| 4,852,768 A | 8/1989 | Bartsch |
| 4,853,521 A | 8/1989 | Claeys et al. |
| 4,854,324 A | 8/1989 | Hirschman et al. |
| 4,863,427 A | 9/1989 | Cocchi |
| 4,869,720 A | 9/1989 | Chernack |
| 4,878,896 A | 11/1989 | Garrison et al. |
| 4,911,695 A | 3/1990 | Lindner |
| 4,923,443 A | 5/1990 | Greenwood et al. |
| 4,929,238 A | 5/1990 | Baum |
| 4,931,043 A | 6/1990 | Ray et al. |
| 4,932,941 A | 6/1990 | Min et al. |
| 4,936,833 A | 6/1990 | Sams |
| 4,943,279 A | 7/1990 | Samiotes et al. |
| 4,966,601 A | 10/1990 | Draenert |
| 4,969,874 A | 11/1990 | Michel et al. |
| 4,973,309 A | 11/1990 | Sultan |
| 4,978,335 A | 12/1990 | Arthur, III |
| 4,988,337 A | 1/1991 | Ito |
| 5,007,904 A | 4/1991 | Densmore et al. |
| 5,019,045 A | 5/1991 | Lee |
| 5,024,663 A | 6/1991 | Yum, II |
| 5,033,650 A | 7/1991 | Colin et al. |
| 5,034,004 A | 7/1991 | Crankshaw |
| 5,047,014 A | 9/1991 | Mosebach et al. |
| 5,059,179 A | 10/1991 | Quatrochi et al. |
| 5,062,832 A | 11/1991 | Seghi |
| 5,078,683 A | 1/1992 | Sancoff et al. |
| 5,084,017 A | 1/1992 | Maffetone |
| 5,085,638 A | 2/1992 | Farbstein et al. |
| 5,085,643 A | 2/1992 | Larkin et al. |
| 5,090,962 A | 2/1992 | Landry, Jr. et al. |
| 5,093,079 A | 3/1992 | Bakaitis et al. |
| 5,094,148 A | 3/1992 | Haber et al. |
| 5,104,374 A | 4/1992 | Bishko et al. |
| 5,106,372 A | 4/1992 | Ranford |
| 5,106,379 A | 4/1992 | Leap |
| 5,122,118 A | 6/1992 | Haber et al. |
| 5,135,507 A | 8/1992 | Haber et al. |
| 5,147,311 A | 9/1992 | Pickhard |
| 5,153,827 A | 10/1992 | Coutre et al. |
| 5,176,642 A | 1/1993 | Clement |
| 5,181,912 A | 1/1993 | Hammett |
| 5,226,897 A | 7/1993 | Nevens et al. |
| 5,236,416 A | 8/1993 | McDaniel et al. |
| 5,242,408 A | 9/1993 | Jhuboo et al. |
| 5,246,423 A | 9/1993 | Farkas |
| 5,254,086 A | 10/1993 | Palmer et al. |
| 5,254,101 A | 10/1993 | Trombley, III |
| 5,256,154 A | 10/1993 | Liebert et al. |
| 5,256,157 A | 10/1993 | Samiotes et al. |
| 5,269,762 A | 12/1993 | Armbruster et al. |
| 5,275,582 A | 1/1994 | Wimmer |
| 5,279,569 A | 1/1994 | Neer et al. |
| 5,282,792 A | 2/1994 | Imbert |
| 5,282,858 A | 2/1994 | Bisch et al. |
| 5,300,031 A | 4/1994 | Neer et al. |
| 5,308,330 A | 5/1994 | Grimard |
| 5,314,415 A | 5/1994 | Liebert et al. |
| 5,317,506 A | 5/1994 | Coutre et al. |
| 5,324,273 A | 6/1994 | Discko, Jr. |
| 5,336,189 A | 8/1994 | Sealfon |
| 5,338,309 A | 8/1994 | Imbert |
| 5,342,298 A | 8/1994 | Michaels et al. |
| 5,353,691 A | 10/1994 | Haber et al. |
| 5,354,287 A | 10/1994 | Wacks |
| 5,356,375 A | 10/1994 | Higley |
| 5,356,393 A | 10/1994 | Haber et al. |
| 5,373,684 A | 12/1994 | Vacca |
| 5,380,285 A | 1/1995 | Jenson |
| 5,383,858 A | 1/1995 | Reilly et al. |
| 5,397,313 A | 3/1995 | Gross |
| 5,411,488 A | 5/1995 | Pagay et al. |
| 5,413,563 A | 5/1995 | Basile et al. |
| 5,425,716 A | 6/1995 | Kawasaki et al. |

(56) References Cited

U.S. PATENT DOCUMENTS

| | | | |
|---|---|---|---|
| 5,429,602 A | 7/1995 | Hauser |
| 5,429,611 A | 7/1995 | Rait |
| 5,431,627 A | 7/1995 | Pastrone et al. |
| 5,433,712 A | 7/1995 | Stiles et al. |
| 5,439,452 A | 8/1995 | McCarty |
| 5,445,622 A | 8/1995 | Brown |
| 5,451,211 A | 9/1995 | Neer et al. |
| 5,456,670 A | 10/1995 | Neer et al. |
| 5,478,314 A | 12/1995 | Malenchek |
| 5,484,413 A | 1/1996 | Gevorgian |
| 5,512,054 A | 4/1996 | Morningstar |
| 5,520,653 A | 5/1996 | Reilly et al. |
| 5,531,698 A | 7/1996 | Olsen |
| 5,531,710 A | 7/1996 | Dang et al. |
| 5,533,981 A | 7/1996 | Mandro et al. |
| 5,535,746 A | 7/1996 | Hoover et al. |
| 5,540,660 A | 7/1996 | Jenson |
| 5,545,140 A | 8/1996 | Conero et al. |
| 5,573,515 A | 11/1996 | Wilson et al. |
| 5,593,386 A | 1/1997 | Helldin |
| 5,624,408 A | 4/1997 | Helldin |
| 5,658,261 A | 8/1997 | Neer et al. |
| 5,662,612 A | 9/1997 | Niehoff |
| 5,681,285 A | 10/1997 | Ford et al. |
| 5,681,286 A | 10/1997 | Niehoff |
| 5,683,367 A | 11/1997 | Jordan et al. |
| 5,688,252 A | 11/1997 | Matsuda et al. |
| 5,695,477 A | 12/1997 | Sfikas |
| 5,722,951 A | 3/1998 | Marano |
| 5,735,825 A | 4/1998 | Stevens et al. |
| 5,738,655 A | 4/1998 | Vallelunga et al. |
| 5,738,659 A | 4/1998 | Neer et al. |
| 5,741,227 A | 4/1998 | Sealfon |
| 5,741,232 A | 4/1998 | Reilly et al. |
| 5,779,675 A | 7/1998 | Reilly et al. |
| 5,782,803 A | 7/1998 | Jentzen |
| 5,785,682 A | 7/1998 | Grabenkort |
| 5,795,333 A | 8/1998 | Reilly et al. |
| 5,807,334 A | 9/1998 | Hodosh et al. |
| 5,808,203 A | 9/1998 | Nolan, Jr. et al. |
| 5,827,219 A | 10/1998 | Uber, III et al. |
| 5,827,262 A | 10/1998 | Neftel et al. |
| 5,840,026 A | 11/1998 | Uber, III et al. |
| RE35,979 E | 12/1998 | Reilly et al. |
| 5,865,805 A | 2/1999 | Ziemba |
| 5,873,861 A | 2/1999 | Hitchins et al. |
| 5,879,336 A | 3/1999 | Brinon |
| 5,882,343 A | 3/1999 | Wilson et al. |
| 5,899,885 A | 5/1999 | Reilly et al. |
| 5,902,276 A | 5/1999 | Namey, Jr. |
| 5,913,844 A | 6/1999 | Ziemba et al. |
| 5,919,167 A | 7/1999 | Mulhauser et al. |
| 5,938,637 A | 8/1999 | Austin et al. |
| 5,938,639 A | 8/1999 | Reilly et al. |
| 5,944,694 A | 8/1999 | Hitchins et al. |
| 5,947,929 A | 9/1999 | Trull |
| 5,947,935 A | 9/1999 | Rhinehart et al. |
| 5,954,697 A | 9/1999 | Srisathapat et al. |
| 5,954,700 A | 9/1999 | Kovelman |
| 5,997,502 A | 12/1999 | Reilly et al. |
| 5,997,511 A | 12/1999 | Curie et al. |
| 6,004,300 A | 12/1999 | Butcher et al. |
| 6,017,330 A | 1/2000 | Hitchins et al. |
| 6,042,565 A | 3/2000 | Hirschman et al. |
| 6,048,334 A | 4/2000 | Hirschman et al. |
| 6,059,756 A | 5/2000 | Yeh |
| 6,080,136 A | 6/2000 | Trull et al. |
| 6,083,197 A | 7/2000 | Umbaugh |
| 6,083,200 A | 7/2000 | Grimm et al. |
| 6,090,064 A | 7/2000 | Reilly et al. |
| 6,099,502 A | 8/2000 | Duchon et al. |
| 6,129,712 A | 10/2000 | Sudo et al. |
| 6,162,200 A | 12/2000 | Sawa et al. |
| 6,196,999 B1 | 3/2001 | Goethel et al. |
| 6,221,045 B1 | 4/2001 | Duchon et al. |
| 6,224,577 B1 | 5/2001 | Dedola et al. |
| 6,267,749 B1 | 7/2001 | Miklos et al. |
| 6,315,758 B1 | 11/2001 | Neer et al. |
| 6,322,535 B1 | 11/2001 | Hitchins et al. |
| RE37,487 E | 12/2001 | Reilly et al. |
| 6,336,913 B1 | 1/2002 | Spohn et al. |
| 6,339,718 B1 | 1/2002 | Zatezalo et al. |
| 6,345,262 B1 | 2/2002 | Madden |
| 6,432,089 B1 | 8/2002 | Kakimi et al. |
| 6,447,487 B1 | 9/2002 | Cane |
| 6,511,459 B1 | 1/2003 | Fago |
| 6,517,516 B1 | 2/2003 | Caizza |
| 6,533,758 B1 | 3/2003 | Staats et al. |
| 6,582,399 B1 | 6/2003 | Smith et al. |
| 6,585,700 B1 | 7/2003 | Trocki et al. |
| 6,652,489 B2 | 11/2003 | Trocki et al. |
| 6,659,979 B2 | 12/2003 | Neer et al. |
| 6,669,663 B1 | 12/2003 | Thompson |
| 6,733,477 B2 | 5/2004 | Cowan et al. |
| 6,733,478 B2 | 5/2004 | Reilly et al. |
| 6,752,789 B2 | 6/2004 | Duchon et al. |
| 6,764,466 B1 | 7/2004 | Staats et al. |
| 6,808,513 B2 | 10/2004 | Reilly et al. |
| 6,817,990 B2 | 11/2004 | Yap et al. |
| 6,958,053 B1 | 10/2005 | Reilly |
| 7,018,363 B2 | 3/2006 | Cowan et al. |
| 7,029,459 B2 | 4/2006 | Reilly |
| 7,300,417 B1 | 11/2007 | Goethel et al. |
| 7,337,538 B2 | 3/2008 | Moutafis et al. |
| 7,399,293 B2 | 7/2008 | Oyibo et al. |
| 7,419,478 B1 | 9/2008 | Reilly et al. |
| 7,455,659 B2 | 11/2008 | Nemoto et al. |
| 7,462,166 B2 | 12/2008 | Kowan et al. |
| 7,465,290 B2 | 12/2008 | Reilly |
| 7,497,843 B1 | 3/2009 | Castillo et al. |
| 7,501,092 B2 | 3/2009 | Chen |
| 7,540,856 B2 | 6/2009 | Trocki et al. |
| 7,553,294 B2 | 6/2009 | Lazzaro et al. |
| 7,566,326 B2 | 7/2009 | Duchon et al. |
| 7,666,169 B2 | 2/2010 | Cowan et al. |
| 7,682,345 B2 | 3/2010 | Savage |
| 7,803,134 B2 | 9/2010 | Sharifi et al. |
| 7,972,306 B2 | 7/2011 | Shearn |
| 8,012,124 B2 | 9/2011 | Fago et al. |
| 8,012,125 B1 | 9/2011 | Fago et al. |
| 8,038,656 B2 | 10/2011 | Lloyd et al. |
| 8,070,732 B2 | 12/2011 | Rochette |
| 8,105,293 B2 | 1/2012 | Pickhard |
| 8,172,814 B2 | 5/2012 | Cane et al. |
| 8,177,757 B2 | 5/2012 | Nemoto et al. |
| 8,308,689 B2 | 11/2012 | Lewis |
| 8,353,879 B2 | 1/2013 | Goethel et al. |
| 8,475,415 B2 | 7/2013 | Schiller et al. |
| 8,480,631 B2 | 7/2013 | Wotton et al. |
| 8,585,658 B2 | 11/2013 | Forstreuter |
| 8,613,730 B2 | 12/2013 | Hieb et al. |
| 8,628,495 B2 | 1/2014 | Horton et al. |
| 8,721,596 B2 | 5/2014 | Trocki et al. |
| 8,740,854 B2 | 6/2014 | Schiller et al. |
| 8,740,856 B2 | 6/2014 | Quinn et al. |
| 8,845,596 B2 | 9/2014 | Berman et al. |
| 8,851,866 B2 | 10/2014 | Moutafis et al. |
| 8,857,674 B2 | 10/2014 | Nighy et al. |
| 8,864,712 B1 | 10/2014 | Fago et al. |
| 8,926,569 B2 * | 1/2015 | Bisegna ............ A61M 5/31513 604/218 |
| 8,932,255 B1 | 1/2015 | Fago et al. |
| 9,173,995 B1 | 11/2015 | Tucker et al. |
| 9,174,003 B2 | 11/2015 | Cowan et al. |
| 9,199,033 B1 | 12/2015 | Cowan et al. |
| 2001/0047153 A1 | 11/2001 | Trocki et al. |
| 2002/0022807 A1 | 2/2002 | Duchon et al. |
| 2002/0068905 A1 | 6/2002 | Cowan et al. |
| 2002/0128606 A1 | 9/2002 | Cowan et al. |
| 2002/0165491 A1 | 11/2002 | Reilly |
| 2002/0177811 A1 | 11/2002 | Reilly et al. |
| 2003/0004468 A1 | 1/2003 | Righi et al. |
| 2003/0009133 A1 | 1/2003 | Ramey |
| 2003/0060754 A1 | 3/2003 | Reilly et al. |

(56) References Cited

U.S. PATENT DOCUMENTS

| | | |
|---|---|---|
| 2003/0120219 A1 | 6/2003 | Nielsen et al. |
| 2003/0153877 A1 | 8/2003 | Huang et al. |
| 2003/0163089 A1 | 8/2003 | Bynum |
| 2003/0216683 A1 | 11/2003 | Shekalim |
| 2003/0236800 A1 | 12/2003 | Goeltzenleuchter et al. |
| 2004/0006314 A1 | 1/2004 | Campbell et al. |
| 2004/0039368 A1 | 2/2004 | Reilly et al. |
| 2004/0064041 A1 | 4/2004 | Lazzaro et al. |
| 2004/0068223 A1 | 4/2004 | Reilly |
| 2004/0074453 A1 | 4/2004 | Roelle et al. |
| 2004/0116861 A1 | 6/2004 | Trocki et al. |
| 2004/0133153 A1 | 7/2004 | Trocki et al. |
| 2004/0133161 A1 | 7/2004 | Trocki et al. |
| 2004/0133162 A1 | 7/2004 | Trocki et al. |
| 2004/0133183 A1 | 7/2004 | Trocki et al. |
| 2004/0158205 A1 | 8/2004 | Savage |
| 2004/0186437 A1* | 9/2004 | Frenette ............. A61M 5/3129 604/189 |
| 2004/0243022 A1 | 12/2004 | Carney et al. |
| 2005/0015056 A1 | 1/2005 | Duchon et al. |
| 2005/0113754 A1 | 5/2005 | Cowan et al. |
| 2005/0240149 A1 | 10/2005 | Lu |
| 2006/0129104 A1 | 6/2006 | Cowan et al. |
| 2006/0173411 A1 | 8/2006 | Barere |
| 2007/0123830 A1 | 5/2007 | Johannes et al. |
| 2007/0191785 A1 | 8/2007 | Barere et al. |
| 2009/0247957 A1 | 10/2009 | Heutschi |
| 2010/0016796 A1 | 1/2010 | Derichs |
| 2010/0057014 A1 | 3/2010 | Cane et al. |
| 2010/0222674 A1 | 9/2010 | Cowan et al. |
| 2010/0318030 A1 | 12/2010 | Jenkins |
| 2011/0034882 A1 | 2/2011 | Quinn et al. |
| 2011/0178500 A1 | 7/2011 | Shang et al. |
| 2012/0039809 A1 | 2/2012 | Levinson et al. |
| 2012/0184920 A1 | 7/2012 | Okihara et al. |
| 2013/0211325 A1 | 8/2013 | Wang et al. |
| 2013/0317427 A1 | 11/2013 | Brereton et al. |
| 2013/0317480 A1 | 11/2013 | Reber et al. |
| 2013/0338605 A1 | 12/2013 | Chen |
| 2014/0027009 A1 | 1/2014 | Riley et al. |
| 2014/0031763 A1 | 1/2014 | Soma et al. |
| 2014/0094749 A1 | 4/2014 | Cowan et al. |
| 2014/0200483 A1 | 7/2014 | Fojtik |
| 2014/0243746 A1 | 8/2014 | Trocki et al. |
| 2014/0330216 A1 | 11/2014 | Weaver et al. |

FOREIGN PATENT DOCUMENTS

| | | |
|---|---|---|
| DE | 3227417 A1 | 2/1983 |
| DE | 4017920 A1 | 12/1991 |
| DE | 19601214 A1 | 8/1996 |
| DE | 19633530 A1 | 2/1998 |
| EP | 0111724 A2 | 6/1984 |
| EP | 0160303 A2 | 11/1985 |
| EP | 0164904 A2 | 12/1985 |
| EP | 0308380 A2 | 3/1989 |
| EP | 0319275 A1 | 6/1989 |
| EP | 0320168 A1 | 6/1989 |
| EP | 0323321 A1 | 7/1989 |
| EP | 0346950 A2 | 12/1989 |
| EP | 0364010 A2 | 4/1990 |
| EP | 0384657 A1 | 8/1990 |
| EP | 0482677 A1 | 4/1992 |
| EP | 0523343 A1 | 1/1993 |
| EP | 0523434 A1 | 1/1993 |
| EP | 0567944 A1 | 11/1993 |
| EP | 0567945 A1 | 11/1993 |
| EP | 0584531 A2 | 3/1994 |
| EP | 0736306 A1 | 10/1996 |
| EP | 0749757 A2 | 12/1996 |
| EP | 0900573 A2 | 3/1999 |
| EP | 0919251 A2 | 6/1999 |
| EP | 0951306 A2 | 10/1999 |
| EP | 1002551 A2 | 5/2000 |
| EP | 1166807 A1 | 1/2002 |
| EP | 0951306 B1 | 7/2005 |
| EP | 1166807 B1 | 11/2005 |
| GB | 847914 A | 9/1960 |
| GB | 1380873 A | 1/1975 |
| GB | 2108852 A | 5/1983 |
| JP | S61500415 A | 3/1986 |
| JP | S6327770 A | 2/1988 |
| JP | S6368177 A | 3/1988 |
| JP | 2001029466 A | 2/2001 |
| JP | 4462798 B2 | 5/2010 |
| JP | D1398129 | 10/2010 |
| JP | D1398130 | 10/2010 |
| JP | D1400385 | 11/2010 |
| JP | D1400386 | 11/2010 |
| JP | D1400551 | 11/2010 |
| JP | D1400552 | 11/2010 |
| WO | 8002376 A1 | 11/1980 |
| WO | 8500292 A1 | 1/1985 |
| WO | 8502256 A1 | 5/1985 |
| WO | 8906145 A1 | 7/1989 |
| WO | 8909071 A1 | 10/1989 |
| WO | 8911310 A1 | 11/1989 |
| WO | 9001962 A1 | 3/1990 |
| WO | 9104759 A1 | 4/1991 |
| WO | 9221391 A1 | 12/1992 |
| WO | 9413336 A1 | 6/1994 |
| WO | 9425089 A1 | 11/1994 |
| WO | 9632975 A1 | 10/1996 |
| WO | 9707841 A2 | 3/1997 |
| WO | 9736635 A1 | 10/1997 |
| WO | 9820920 A2 | 5/1998 |
| WO | 9965548 A1 | 12/1999 |
| WO | 0137903 A2 | 5/2001 |
| WO | 0137905 A2 | 5/2001 |
| WO | 0204049 A1 | 1/2002 |
| WO | 03101527 A1 | 12/2003 |
| WO | 2004035289 | 4/2004 |
| WO | 2005053771 A2 | 6/2005 |
| WO | 2007130061 A1 | 11/2007 |
| WO | 2012124028 A1 | 9/2012 |
| WO | 2012155035 A1 | 11/2012 |
| WO | 2015006430 A1 | 1/2015 |

OTHER PUBLICATIONS

Brochure for "Angiomat 6000" of Liebel-Farsheim, 2111 E. Galbraith Road, Cincinnati, OH 45215, © 1987.
Brochure for "Angiomat CT" of Liebel-Farsheim, 2111 E. Galbraith Road, Cincinnati, OH 45215, © 1988.
Brochure for "Cordis Lymphography Injector," Cordis Corporation, Miami, FL 33137 (1972).
Brochure for "PercuPump 1A" of E-Z-Em, Inc, 717 Main Street, Westbury, NY 11590, © 1990.
Brochure for the "The First and Only True Injection System," Medrad Mark V System, Control No. 85106-00-BA-02, Nov. 1988.
Non-Final Office Action dated Mar. 28, 2013 in related U.S. Appl. No. 12/728,869.
FOA dated Mar. 28, 2013 from U.S. Appl. No. 12/728,869.
Injektron 82 MRT User Instructions, Version MR2, CEO535, Med-Tron GmbH(Mar. 10, 1999).
International Search Report & Written Opinion for International Application No. PCT/US2004/039225, ISA/US, dated May 12, 2006.
International Search Report for Counterpart PCT Application No. PCT/US00/32271.
International Search Report for International Application No. PCT/AU01/00830, dated Nov. 1, 2001.
International Search Report for International Application No. PCT/US03/17305, dated Oct. 21, 2003.
IPRP dated Jan. 12, 2016 from PCT/US2014/045923.
ISR dated Oct. 30, 2014 from PCT/US2014/045923.
ISR dated May 12, 2006 by PCT/US2004/039225.
ISR from PCT/US97/20122, dated Jun. 30, 1998.
Liebel-Flarsheim company—Angiomat 6000 Digital Injection System Operator's Manual, 600950 Rev 1 (1990); p. 3-6 to 3-8, 4-52 to 4-56.

(56) References Cited

OTHER PUBLICATIONS

Medrad Envision CT Injector Operation Manual, EOM 700E, 92401-T-123 Rev E, Copyright 1995.
Medrad Envision CT Injector Operation Manual, EOM 700E, 92401-T-123 Rev E, pp. 2-10 to 2-11 and pp. 2-30 to 2-35(Copyright 1995).
Medrad, Mark V/Mark V Plus Injector Operation Manual,KMP 805P Rev. B (1990); pp. 1-18 to 1-28, 3-7 to 3-13, 14-1 to 14-4.
Supplementary ESR from EP 01949108 dated Apr. 13, 2007.
Supplementary ESR from EP 01949108 dated Apr. 25, 2007.
Supplementary Partial European Search Report for EP 01949108 dated Apr. 13, 2007.
Supplementary Partial European Search Report for EP 01949108 dated Apr. 25, 2007.
The European Search Report dated Apr. 27, 2015 from corresponding EP Application No. EP14174725.
The International Preliminary Report on Patentability dated Apr. 9, 2015 from corresponding PCT Application No. PCT/US2013/061384.
The International Search Report from corresponding PCT Application PCT/US2013/061384 dated Feb. 20, 2014.
U.S. Appl. No. 09/448,835, filed Nov. 24, 1999.
U.S. Appl. No. 09/731,108, filed Dec. 6, 2000.
U.S. Appl. No. 10/159,592, filed May 30, 2002.
U.S. Appl. No. 10/166,848, filed Jun. 10, 2002.
U.S. Appl. No. 10/174,631, filed Jun. 19, 2002.
U.S. Appl. No. 10/174,639, filed Jun. 19, 2002.
U.S. Appl. No. 10/287,167, filed Nov. 4, 2002.
U.S. Appl. No. 10/380,188, filed Mar. 10, 2003.
U.S. Appl. No. 10/606,157, filed Jun. 25, 2003.
U.S. Appl. No. 10/606,157, filed Nov. 25, 2003.
U.S. Appl. No. 10/619,137, filed Jul. 14, 2003.
U.S. Appl. No. 10/668,643, filed Sep. 23, 2003.
U.S. Appl. No. 10/668,673, filed Sep. 23, 2003.
U.S. Appl. No. 10/669,144, filed Sep. 23, 2003.
U.S. Appl. No. 10/669,148, filed Sep. 23, 2003.
U.S. Appl. No. 10/670,154, filed Sep. 23, 2003.
U.S. Appl. No. 10/722,370, filed Nov. 25, 2003.
WO dated Oct. 30, 2014 from PCT/US2014/045923.

\* cited by examiner

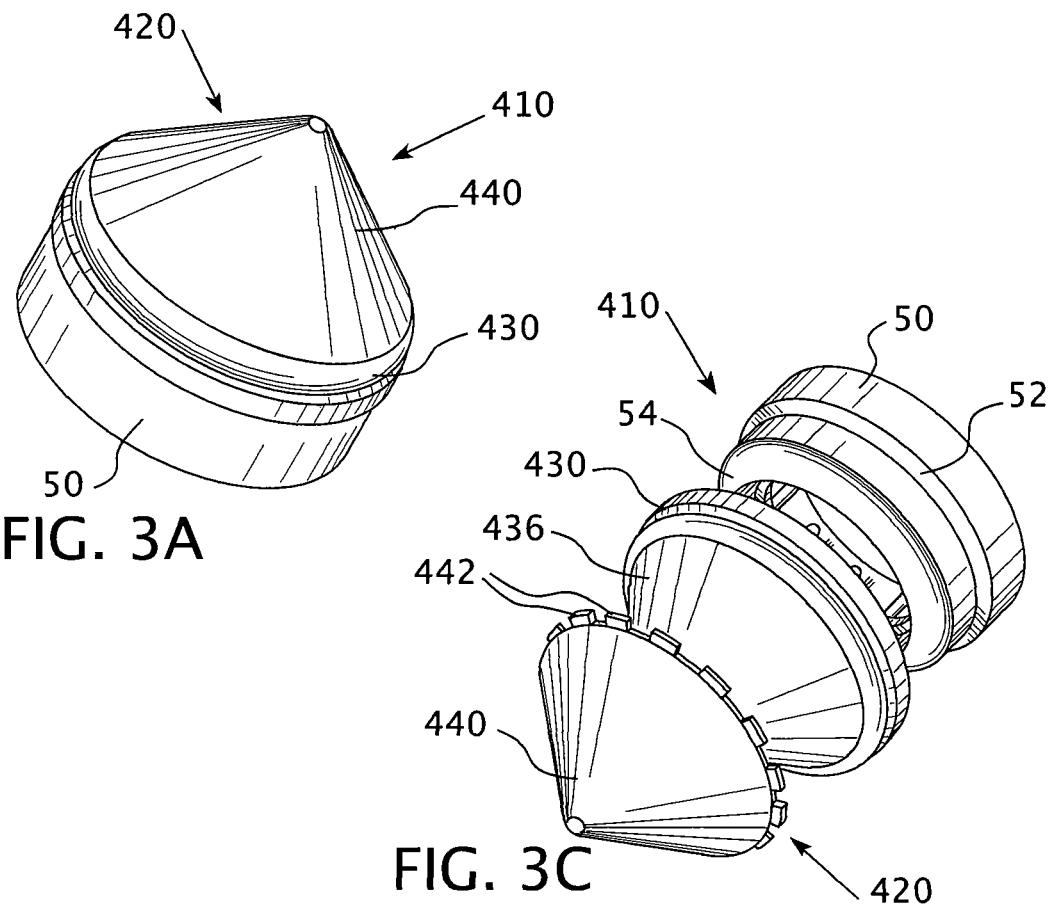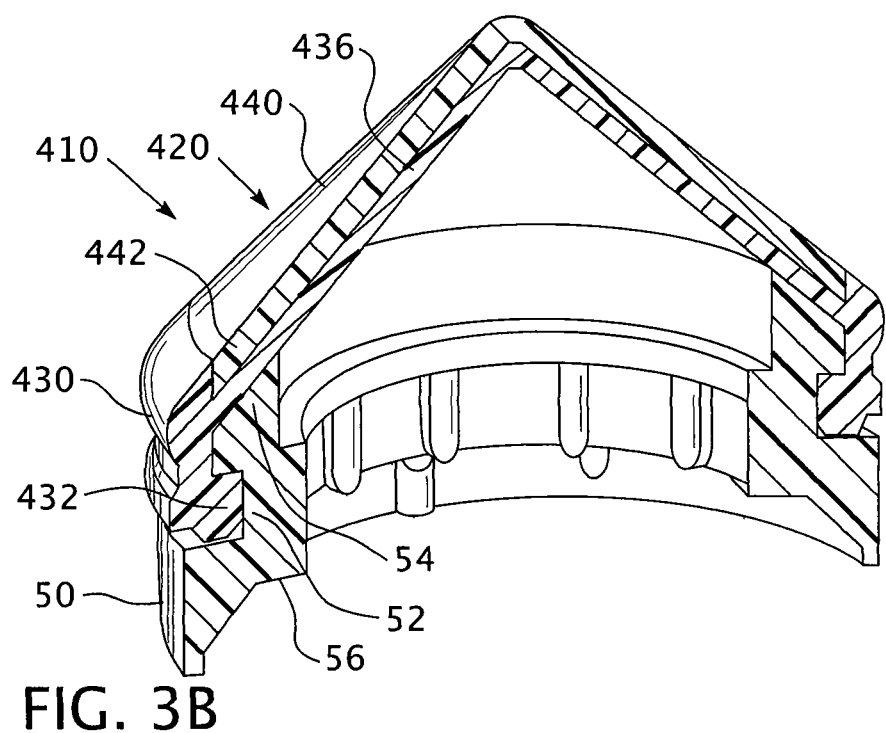

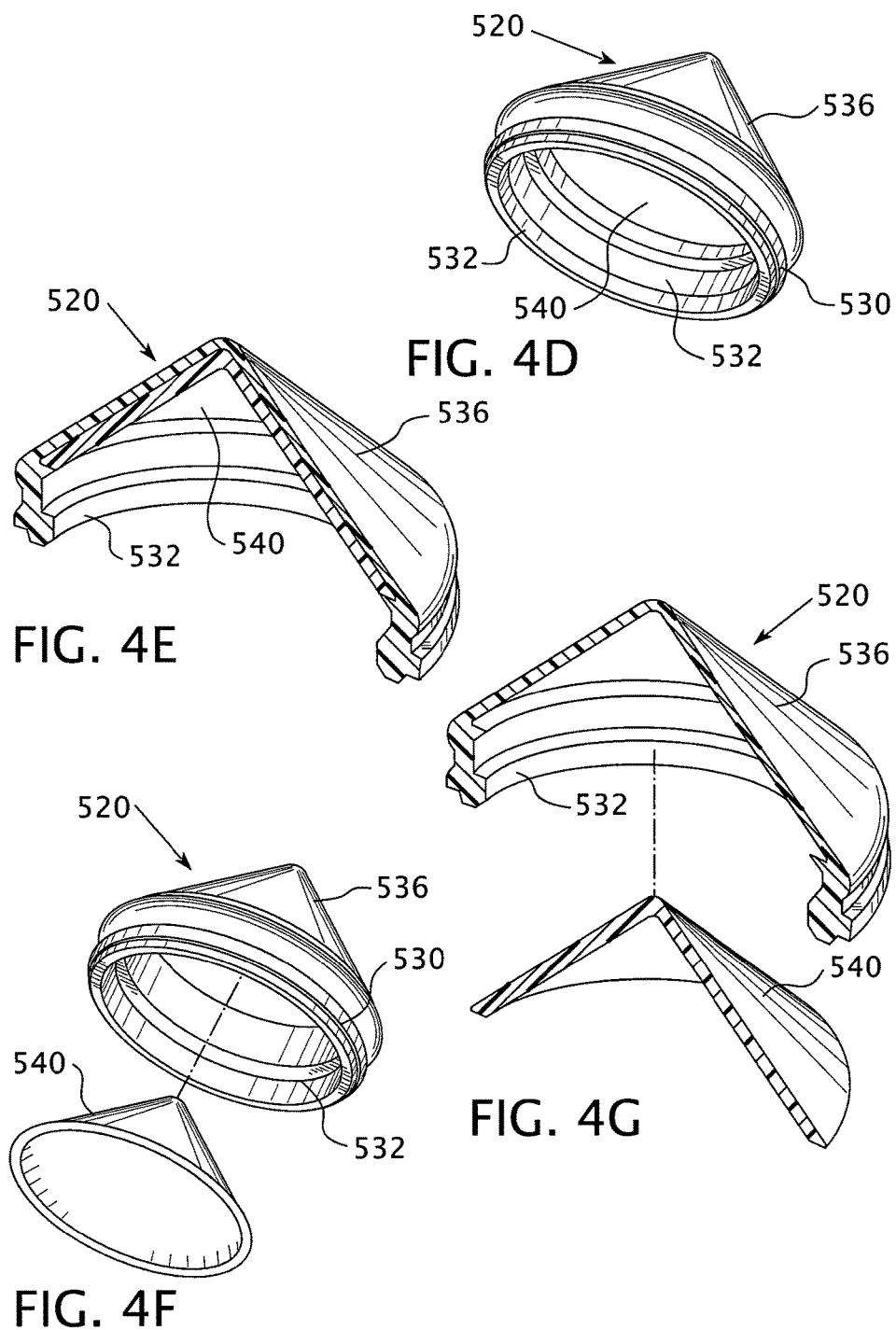

PLUNGER COVERS AND PLUNGERS FOR USE IN SYRINGES

CROSS REFERENCE TO RELATED APPLICATION

This application is divisional application of 11/686,000, filed Mar. 14, 2007, which claims priority to U.S. Provisional Application Ser. No. 60/782,623, filed on Mar. 15, 2006, the contents of which are hereby incorporated by reference.

BACKGROUND OF THE INVENTION

The present invention relates generally to plunger covers and to plungers for use in syringes and to methods of fabrication of plunger covers and plungers for use in syringes, and particularly, to plunger covers and to plungers for use in syringes to inject fluids into a patient and to methods of fabrication thereof.

A number of injector-actuated syringes and powered injectors for use in medical procedures such as angiography, computed tomography, ultrasound and magnetic resonance imaging (MRI) have been developed. U.S. Pat. No. 4,006,736, the disclosure of which is incorporated herein by reference, for example, discloses an injector and syringe for injecting fluid into the vascular system of a human being or an animal. Typically, such injectors comprise drive members such as pistons that operatively connect to a syringe plunger. For example, U.S. Pat. No. 4,677,980, the disclosure of which is incorporated herein by reference, discloses an angiographic injector and syringe wherein the drive member of the injector can be connected to, or disconnected from, the syringe plunger at any point along the travel path of the plunger via a releasable mechanism. A front-loading syringe and injector system is also disclosed in U.S. Pat. No. 5,383,858, the disclosure of which is incorporated herein by reference. Front-loading syringes and syringe plungers for use therewith are also disclosed in U.S. Pat. Nos. 6,585,700 and 6,224,577, the disclosures of which are incorporated herein by reference.

Forward, sliding motion of the syringe plunger within the syringe barrel pressurizes the fluid within the syringe, and the pressurized fluid is injected into that patient via a syringe outlet. A common method of manufacturing syringe plungers adapted, for example, for use in connection with powered injectors is to place an elastomeric, sealing plunger cover over a rigid base. Such rubber covers can, for example, be manufactured by a vulcanization compression molding process. The rubber covers can, for example, be molded into a sheet and then manually hand cut (through a cutting die) from the sheet. Once cut, the rubber covers are, for example, washed in a silicone wash and then assembled onto a plunger base for insertion into a syringe. The process results in substantial material waste and can also result in substantial manufacturing costs and time.

U.S. Pat. No. 5,902,276, the disclosure of which in incorporated herein by reference, discloses a syringe plunger that is formed by a two-shot molding process. A hard plastic core is first formed in a first mold. Subsequently, the distal portion of the hard plastic core is overmolded with a soft rubber plunger cover in a second mold. The second overmolding can occur in the second mold while the core is still cooling to effect molecular bonding of the rubber of the cover with the as-yet uncured plastic of the core.

WO 2004/035289, the disclosure of which is incorporated herein by reference, a copy of which is included herewith and made a part hereof, discloses a method of manufacturing plungers for medical syringes wherein the plunger includes at least two parts. In that regard, the plunger includes a plunger body made of a first plastic and a piston body (in the form of a sealing cover) at the front of the plunger body made of a second plastic. The second plastic (an elastomer) is softer than the first plastic (a generally rigid plastic) of the plunger cover. In forming the plunger, the piston body is first formed by injection molding. Then, the plunger body (or a part thereof) is injected molded against or over the piston body.

Although a number of syringe plungers and methods of fabrication or manufacture of syringe plungers have been developed, it is desirable to develop improved syringe plungers and methods of fabrication of syringe plungers.

SUMMARY OF THE INVENTION

In one aspect, the present invention provides a plunger cover for use with a syringe including a sealing portion adapted to form a seal with the syringe and a central portion adapted to contact fluid within the syringe. The central portion can, for example, be more rigid than the sealing portion. The sealing portion and the central portion are connected in an overmolding process. The sealing portion can, for example, be formed from a thermoplastic elastomer or a thermoplastic polyurethane. The central portion can, for example, be formed from polypropylene, acrylonitrile butadiene styrene, polycarbonate or copolymers thereof.

In several embodiments, the sealing portion is injection molded first and the central portion is injection overmolded thereon. In other embodiments, the central portion is injection molded first and the sealing portion is injection overmolded thereon. In several preferred embodiments, the sealing portion is injection molded first and the central portion is injection overmolded thereon. The material for the sealing portion and the material for the central portion can be selected so that molecular bonding occurs between the sealing portion and the central portion.

In another aspect, the present provides a plunger for use with a syringe including a plunger cover including a sealing portion adapted to form a seal with the syringe and a central portion adapted to contact fluid within the syringe as described above. The central portion can, for example, be more rigid than the sealing portion. The sealing portion and the central portion are connected in an overmolding process. The plunger further includes a support attached to the plunger cover.

The sealing portion can, for example, includes a radially inward projecting flange that is seated within a seating formed on the support to connect the plunger cover to the support. The support can, for example, include a forward surface adapted to abut the plunger cover to prevent rearward motion of the central portion relative to the support.

In another aspect, the present invention provides a syringe including a syringe body and a plunger slidably positioned within the syringe body. As described above, the plunger includes a plunger cover including a sealing portion adapted to form a seal with the syringe and a central portion adapted to contact fluid within the syringe. The central portion can, for example, be more rigid than the sealing portion. The sealing portion and the central portion are connected in an overmolding process. The plunger further includes a support attached to the plunger cover.

In a further aspect, the present invention provides a method of fabricating a plunger cover for use in a syringe, including: connecting a sealing portion adapted to form a seal with the syringe and a central portion adapted to contact fluid within the syringe in an overmolding process, the central portion being more rigid than the sealing portion. The sealing portion can, for example, be injection molded first and the central portion is injection overmolded thereon. Alternatively, the central portion can be injection molded first and the sealing portion is injection overmolded thereon.

In another aspect, the present invention provides a plunger cover for use with a syringe including a sealing portion adapted to form a seal with the syringe and a central portion adapted to contact fluid within the syringe. The central portion has at least one physiochemical property that differs from the sealing portion. The sealing portion and the central portion are connected in an overmolding process.

In another aspect, the present invention provides a plunger cover for use with a syringe including a sealing portion adapted to form a seal with the syringe and a central portion. The central portion is more rigid than the sealing portion. The sealing portion and the central portion being connected in an overmolding process. In one embodiment, the central portion is positioned forward of at least a portion of the sealing portion and is adapted to contact fluid within the syringe. In another embodiment, the central portion is positioned rearward of a generally central section of the sealing portion and does not contact fluid within the syringe. The central portion can, for example, be overmolded upon the sealing portion. Alternatively, the central portion can be injection molded first and the sealing portion is injection overmolded thereon.

In still a further aspect, the present invention provides a plunger for use with a syringe including a sealing portion adapted to form a seal with the syringe and a central portion adapted to contact fluid within the syringe. The central portion is, for example, more rigid than the sealing portion. The sealing portion and the central portion are connected in an overmolding process. The sealing portion can, for example, be adapted to form an operative connection with a drive member.

The present invention, along with the attributes and attendant advantages thereof, will best be appreciated and understood in view of the following detailed description taken in conjunction with the accompanying drawings.

BRIEF DESCRIPTION OF THE DRAWINGS

FIG. 3A illustrates a perspective view of another embodiment of a plunger of the present invention.

FIG. 3B illustrates a perspective cutaway view of the plunger of FIG. 3A.

FIG. 3C illustrates a front perspective, exploded view of the plunger of FIG. 3A wherein the plunger cover is disconnected from the base and the sealing portion of the plunger cover is separated from the central or cone portion of the plunger cover.

FIG. 4D illustrates a rear perspective view of the plunger cover of the plunger FIG. 4A.

FIG. 4E illustrates a front, cutaway perspective view of the plunger cover of the plunger of FIG. 4A.

FIG. 4F illustrates a rear perspective, exploded view of the plunger cover of the plunger of FIG. 4A wherein the sealing portion of the plunger cover is separated from the central or cone portion of the plunger cover.

FIG. 4G illustrates a front perspective, exploded view of the plunger cover of the plunger of FIG. 4A wherein the sealing portion of the plunger cover is separated from the central or cone portion of the plunger cover.

DETAILED DESCRIPTION OF THE INVENTION

Figure 1A:
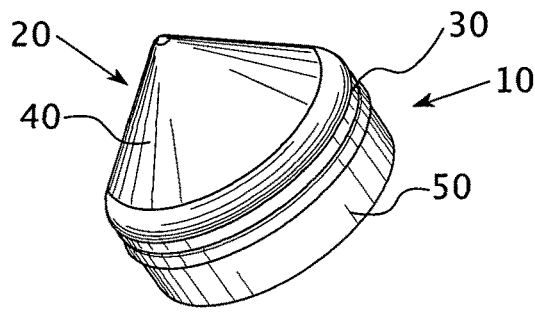
FIG. 1A illustrates a perspective view of an embodiment of a plunger of the present invention.
Figure 1B:
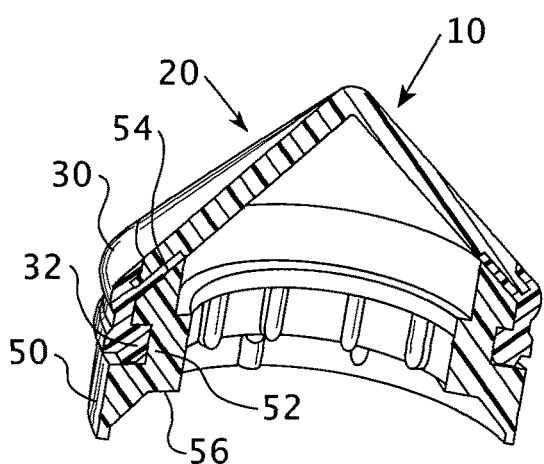
FIG. 1B illustrates a perspective cutaway view of the plunger of FIG. 1A.
Figure 1C:
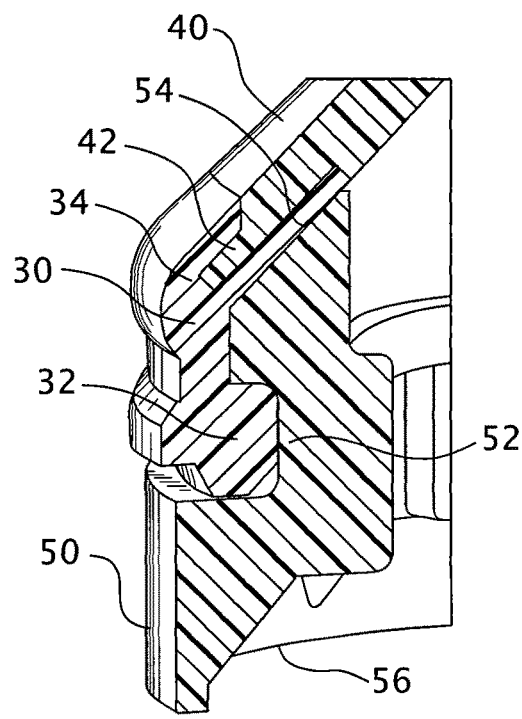
FIG. 1C illustrates an enlarged cutaway view of a portion of the plunger of FIG. 1A.
Figure 1D:
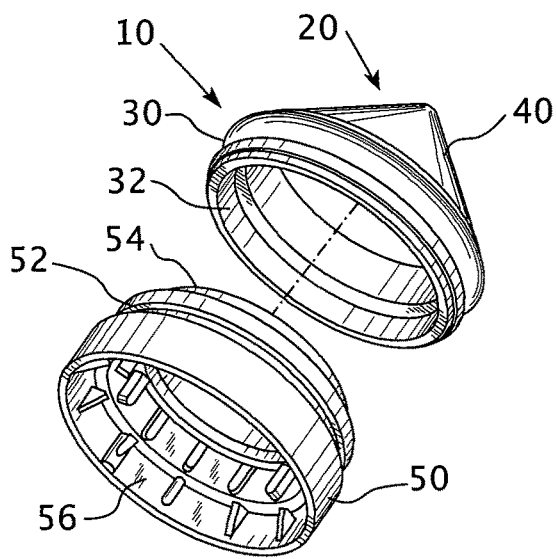
FIG. 1D illustrates a rear perspective, exploded view of the plunger of FIG. 1A wherein the plunger cover is disconnected from the base.
Figure 1E:
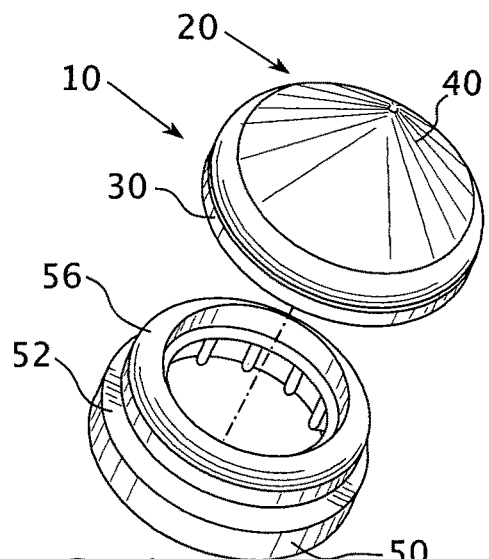
FIG. 1E illustrates a front perspective, exploded view of the plunger of FIG. 1A wherein the plunger cover is disconnected from the base.
Figure 1F:
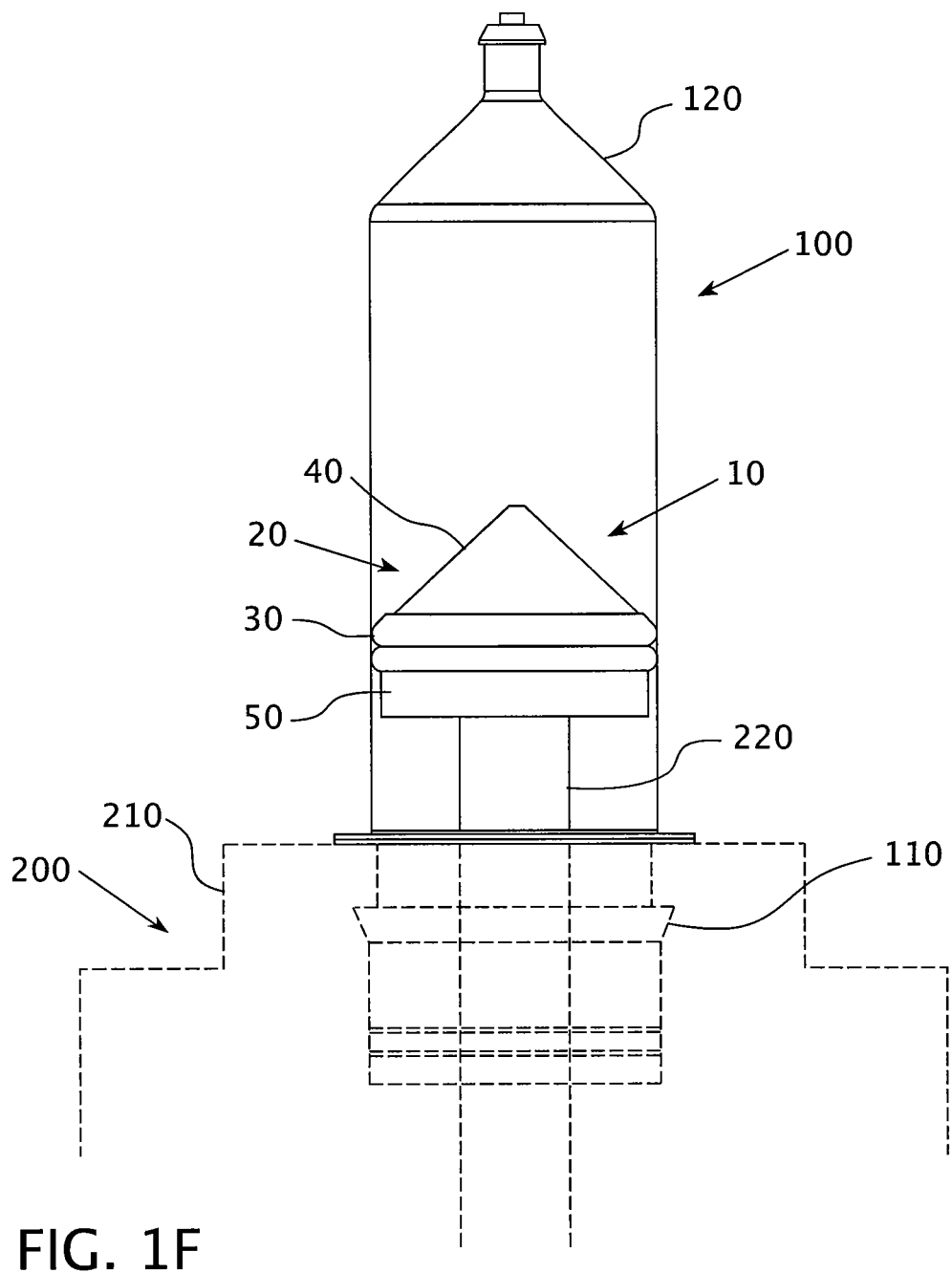
FIG. 1F illustrates a side schematic view of the plunger of FIG. 1A slidably positioned within a syringe that is removably attached to a powered injector.

One embodiment of a plunger 10 of the present invention is illustrated in FIG. 1A through 1F. As illustrated, for example, in FIGS. 1D and 1E, plunger 10 includes a plunger cover 20 that contacts the fluid within a syringe 100 (see FIG. 1F) and forms a seal with the inner wall of the generally cylindrical barrel of syringe 100. Syringe 100 is adapted to be removably connected to an injector 200 via, for example, a retaining flange 110 on syringe 100 the cooperates with a retainer on a syringe interface 210 of injector 200. Injector 200 includes a drive member or piston 220 moveable in a reciprocal manner to pressurize fluid within syringe 100.

Plunger cover 20 includes a sealing section 30 formed, for example, from an elastomeric material suitable to form a sealing engagement with the inner wall of syringe 100. Plunger cover 20 further includes a generally central portion 40 formed from a generally rigid polymeric material. In the embodiment of FIG. 1A through 1G, central portion 40 has a conical shape adapted to contact the injection fluid and to mate generally with a conical transition region 120 of syringe 100. Plunger 10 further includes a base, support or support ring 50 to which plunger cover 20 is attached. In that regard, elastomeric sealing portion 30 includes a radially inward projecting flange 32 that is seatable within a seating 52 formed in base 50. Base 50 further includes a forward surface 54 that is shaped to contact and mate generally with a rearward surface of plunger cover 20 and to provide support for plunger cover 20. In that regard, abutment of forward surface 54 with plunger cover 20 limits or prevents rearward motion of plunger cover 20 relative to base or support 50. To limit such rearward motion, forward surface 54 preferably contacts a portion of plunger cover 20 so that at least a portion of rigid central conical portion is in alignment with at least a portion forward surface 54. A rearward surface 56 of base 50 is adapted to be contacted by piston 220.

Preferably, plunger cover 20 is formed in an overmolding process such as disclosed in WO 2004/035289. In an injection overmolding process, an injection molding machine is used which includes a heated screw and barrel that melt polymer to a liquid state. In general, an injection molding machine pushes/injects the molten polymer through a heated manifold system into a mold. Once the polymer is inside the mold, it is cooled to a final shape (as determined by the internal dimensions of the mold), and then ejected. In general, waste material associated with injection molding overmolding processes is less than associated with many other manufacturing processes for multi-component articles. Moreover, the overmolding process can be operated automatically. Once the part is formed and cooled, no additional operations are required.

In one embodiment of an overmolding process of the present invention, sealing portion 30 of plunger cover 20 is first injection molded in an appropriately shaped mold. Examples of materials suitable for use in injection molding sealing portion 30 include thermoplastic elastomers (TPE) or thermoplastic polyurethanes (TPU). In general, a thermoplastic elastomer or thermoplastic rubber (TPR) is a polymer compound or blend which exhibits a thermoplastic character above it's melt temperature that enables it to be shaped into a fabricated article. Within the design temperature range, the material exhibits elastomeric behavior. In one embodiment, sealing portion 30 was fabricated from SANTOPRENE®, a TPE available, for example, from Advanced Elastomer Systems, L.P. of Akron, Ohio. After injection molding of sealing portion 30, central portion 40 of plunger cover 20 was molded over the TPE/TPU material of molded sealing portion 30. Central portion 40 was injection overmolded with a rigid polymeric material (for example, polypropylene, acrylonitrile butadiene styrene (ABS) or polycarbonate (PC)). Copolymers such as, for example, a PC/ABS copolymer are also suitable for use herein. The overmolding process, for example, can be done in a manual transferred operation or automatically within the same molding machine. In an insert molding process, for example, sealing portion 30 is molded first. Sealing portion 30 is then inserted into another process/mold and is overmolded over with another polymer.

The overmolded polymer does not have to be rigid polymer. The overmolded polymer can, for example, be another polymer having different physiochemical properties. A multilayered plunger/plunger cover can thereby be formed. For example, a less expensive material can be used on an inner portion of the plunger/plunger cover and a more expensive material (having better functionality—for example, a medical grade material) can be used on the outside of the plunger/plunger cover.

As known in the overmolding arts, a molecular bond can be formed between the material of sealing portion 30 and central portion 40. In addition to overmolding central portion 40 upon sealing portion 30, sealing portion 30 can be overmolded upon central portion 40. Control of the strength of the molecular bond can be achieved by appropriate selection of materials. In that regard, as known in the injection molding arts, to form a stronger molecular bond, the melt temperature of the first injected material is preferably similar to the melt temperature of the second, overmolded material. Materials that have dissimilar melt temperatures typically result in a weak molecular bond.

In addition to molecular bonding, sealing portion 30 and central portion 40 can be shaped to interconnect mechanically to add structural integrity to the connection therebetween. For example, elastomeric sealing portion 30 can be formed with a seating or groove 34 into which an extending portion 42 of central conical section 40 (see, for example, FIG. 1C) extends during the overmolding process to provide mechanical interconnection and structural integrity to the connection between sealing portion 30 and central portion 40.

As described above, elastomeric sealing portion 30 mates and form a sealing engagement with the syringe barrel wall to seal fluid inside syringe 100 As compared to plunger covers formed generally entirely of an elastomeric material via, for example, a compression molding process, central conical portion 40, formed from a relatively rigid polymeric material, provides additional structural integrity. The increased structural integrity also reduces compliance. Overmolded plunger cover 20 is a separate component of the plunger and can be assembled in various configurations (for example, with different bases or supports or without a base or support). The design and manufacturing methods associated with plunger 10 reduce manufacturing costs, while maintaining functionality. The manufacturing process provides the capability of customization of plunger cover 20. For example, colorants can be applied to the rigid polymer cone for various purposes. Moreover, the overall shape of the plunger cover can readily be altered for use with different syringes. For example, the forward portion of the plunger cover can have a conical, hemispherical, flat or other shape to mate with a correspondingly shaped syringe. In general, plunger 10 can replace currently available compression molded plunger covers in currently available plunger designs while maintaining or improving functionality of those plunger designs.

Figure 2A:
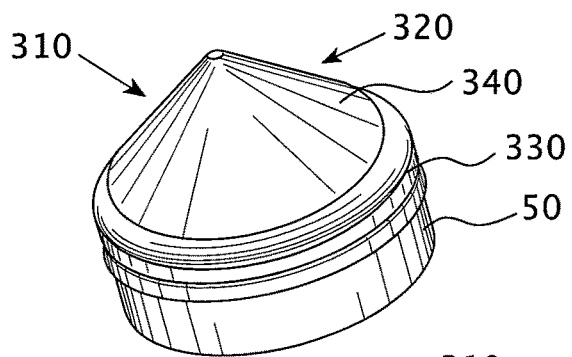
FIG. 2A illustrates a perspective view of another embodiment of a plunger of the present invention.
Figure 2B:
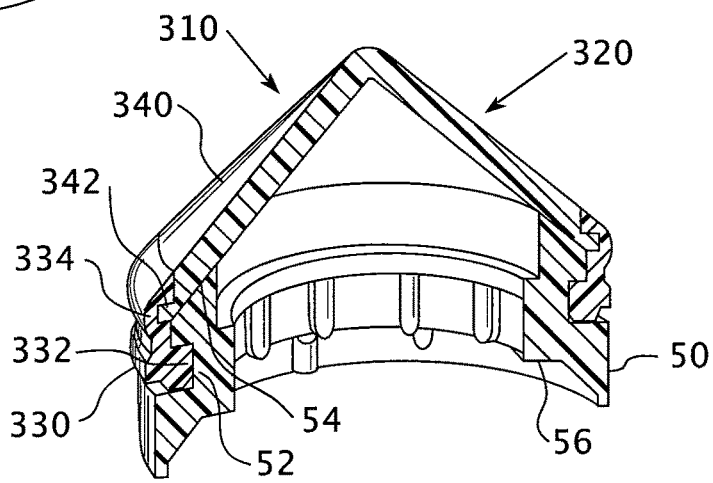
FIG. 2B illustrates a perspective cutaway view of the plunger of FIG. 2A.
Figure 2C:
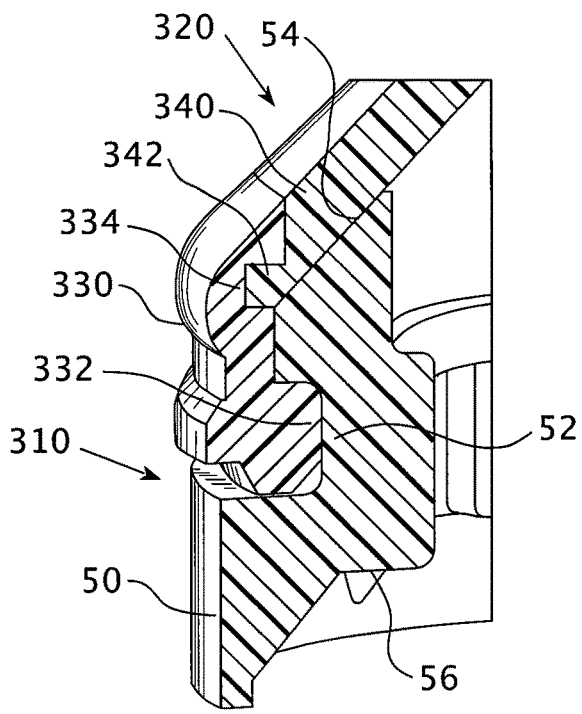
FIG. 2C illustrates an enlarged perspective cutaway view of a portion of the plunger of FIG. 2A.
Figure 2D:
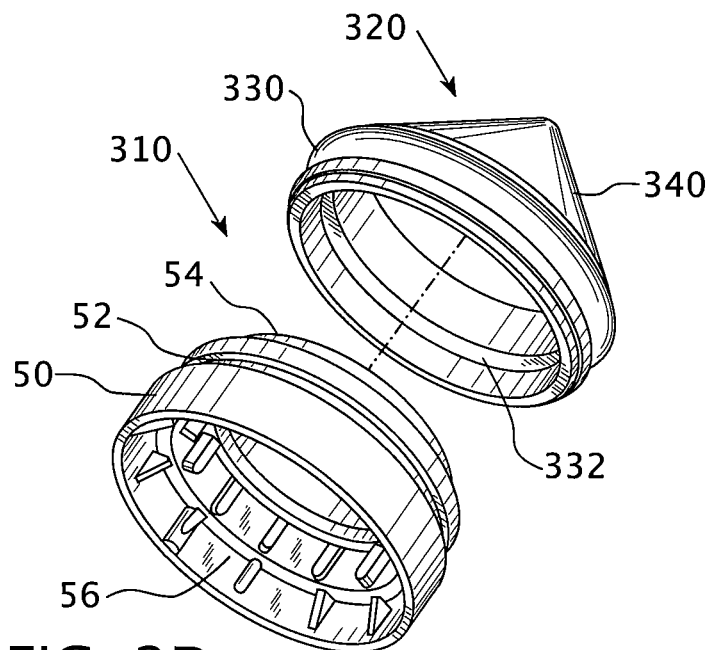
FIG. 2D illustrates a rear perspective, exploded view of the plunger of FIG. 2A wherein the plunger cover is disconnected from the base.
Figure 2E:
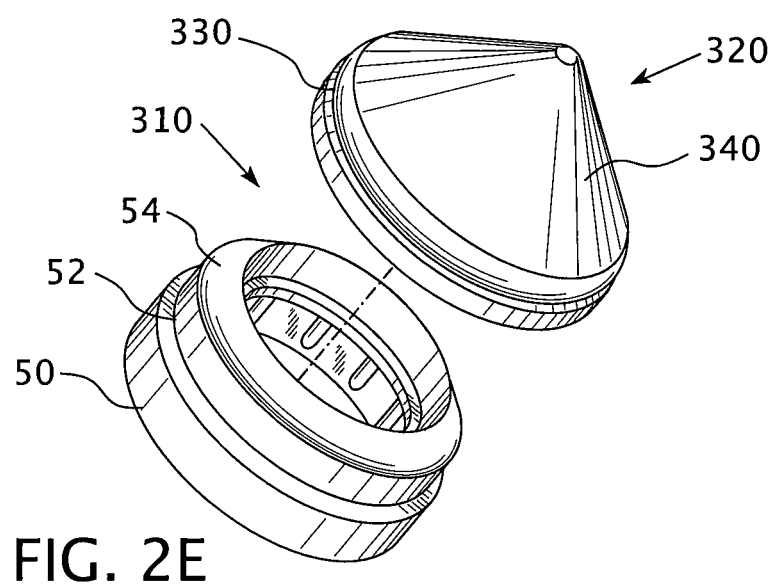
FIG. 2E illustrates a front perspective, exploded view of the plunger of FIG. 2A wherein the plunger cover is disconnected from the base.

FIGS. 2A through 2E illustrate another embodiment of a plunger 310 of the present invention which is similar in design, operation and manufacture to plunger 10. In plunger 310, base or support 50 is identical to that used in plunger 10. Plunger cover 320 differs from plunger cover 20, for example, in the from of the mechanical interconnection between sealing portion 330 and central portion 340, which in the embodiment of FIGS. 2A through 2E is generally conical in shape. In that regard, For example, elastomeric sealing portion 330 is formed with a seating or groove 334 that is somewhat shorter in length than seating 34 of sealing portion 30. Similar to central portion 40, central portion 340 includes an extending portion 342 which extends into seating 334 during the overmolding process. In the embodiment of FIGS. 2A through 2E, forward surface 54 of base 50 contacts a rearward surface of central conical portion 340 directly (without any section of sealing portion 330 therebetween).

Figure 3D:
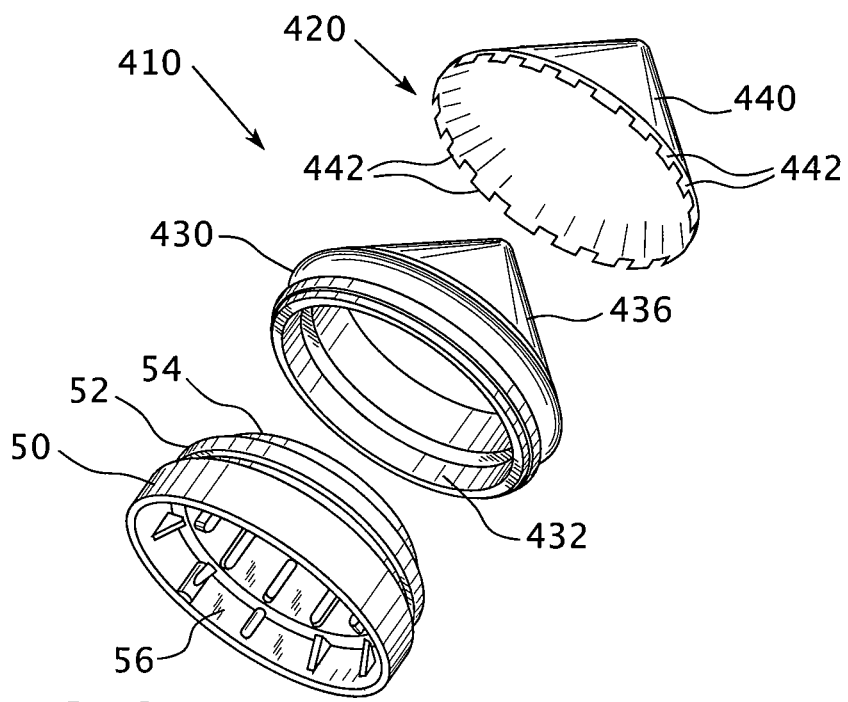
FIG. 3D illustrates a rear perspective, exploded view of the plunger of FIG. 3A wherein the plunger cover is disconnected from the base and the sealing portion of the plunger cover is separated from the central or cone portion of the plunger cover.
Figure 3E:
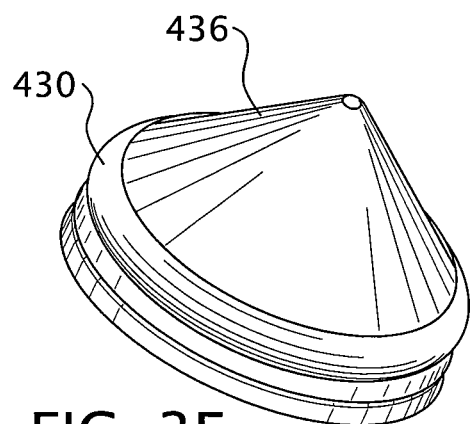
FIG. 3E illustrates a front perspective view of the sealing portion of the plunger cover of FIG. 3A.
Figure 3F:
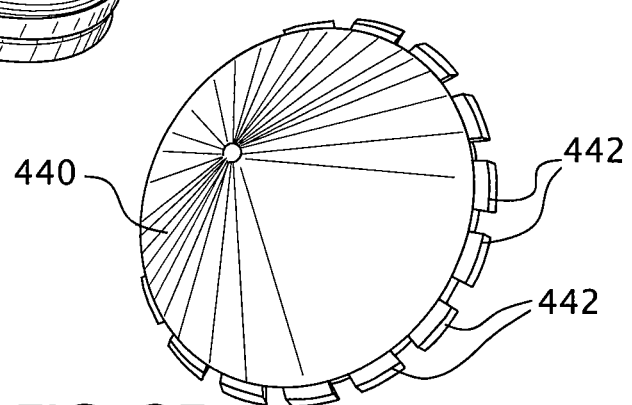
FIG. 3F illustrates a front perspective view of the central or cone portion of the plunger of FIG. 3A.

FIGS. 3A through 3F illustrate another embodiment of a plunger 410 of the present invention. Similar to plungers 10 and 310, plunger 410 includes a plunger cover 420, which includes a sealing section 430 formed, for example, from an elastomeric material such as a TPE/TPU material. Plunger cover 420 further includes a generally conical central portion 440 formed from a generally rigid polymeric material, preferably in an overmolding process. Plunger 410 further includes base or support ring 50 as described above to which plunger cover 420 is attached. In that regard, elastomeric sealing portion 430 includes a radially inward projecting flange 432 that is seatable within seating 52 formed in base 50. As with other embodiments of the present invention, however, plunger cover 420 is readily adjusted in shape and dimension to mate with a desired support.

Central portion 440 can include extending tabs 442 which can assist in forming a secure interconnection between central portion 440 and sealing portion 430. In general, such mechanical interconnections are optional in all overmolding embodiments of the present invention. In the embodiment of FIGS. 3A through 3F sealing portion 430 includes a generally conical central section 436 appropriately dimensioned such that the forward surface of central section 436 of sealing portion 430 mates with the rearward surface of rigid conical central portion 440. Central section 436 of sealing portion 430 can, for example, provide greater area for molecular bonding between central portion 440 and sealing portion 430 during the overmolding process. Central section 436 of sealing portion 430 can also provide for more effective molding of plunger cover 420 in that injection gates for sealing portion 430 and central portion 440 can have the same general location.

Figure 4A:
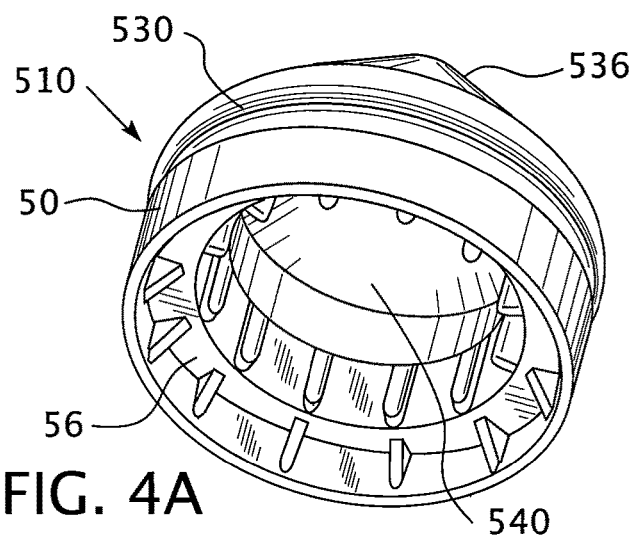
FIG. 4A illustrates a perspective view of another embodiment of a plunger of the present invention.
Figure 4B:
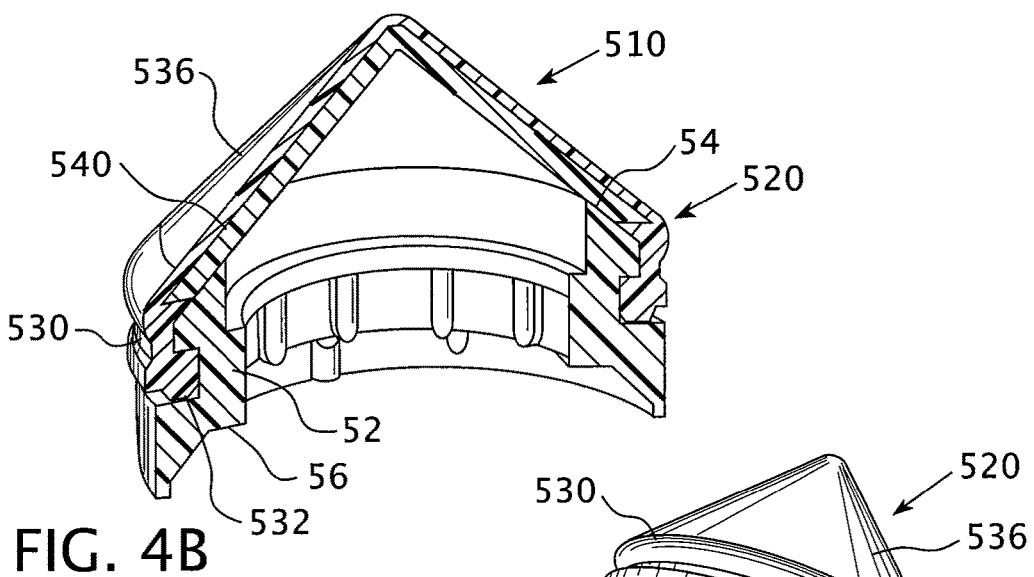
FIG. 4B illustrates a perspective cutaway view of the plunger of FIG. 3A.
Figure 4C:
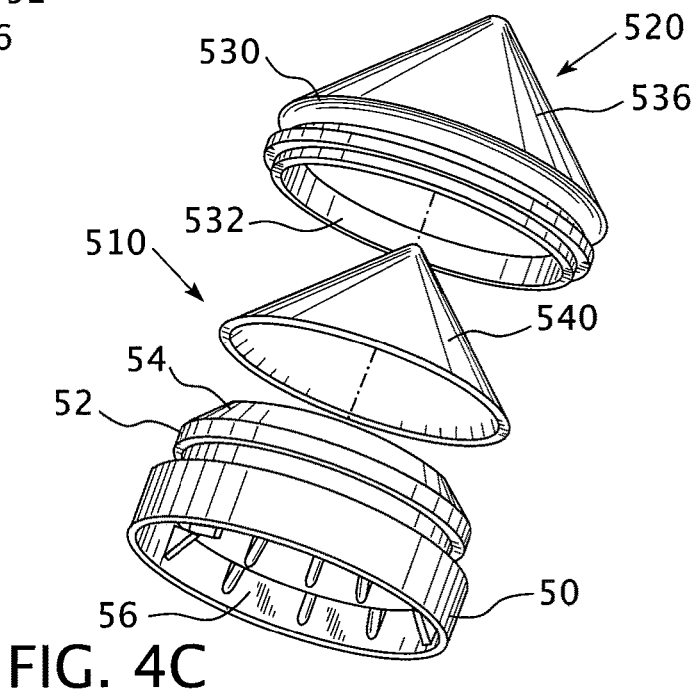
FIG. 4C illustrates a front perspective, exploded view of the plunger of FIG. 4A wherein the plunger cover is disconnected from the base and the sealing portion of the plunger cover is separated from the central or cone portion of the plunger cover.

FIGS. 4A through 4G illustrate another embodiment of a plunger 510 of the present invention. Similar to plunger 410, plunger 510 includes a plunger cover 520, which includes a sealing portion 530 formed, for example, from an elastomeric material such as a TPE/TPU material. Plunger cover 520 further includes a generally conical central portion 540 formed from a generally rigid polymeric material, preferably in an overmolding process. Plunger 510 further includes base or support ring 50 as described above to which plunger cover 520 is attached. In that regard, elastomeric sealing portion 530 includes a radially inward projecting flange 532 that is seatable within seating 52 formed in base 50. As with other embodiments of the present invention, however, plunger cover 520 is readily adjusted in shape and dimension to mate with a desired support.

In the embodiment of FIGS. 4A through 4G central portion 540 is positioned to the rear of a generally conical central section 536 of sealing portion 430. In this embodiment, rigid central portion 540 does not contact the injection fluid, but still provides structural integrity to plunger cover 520.

Figure 5A:
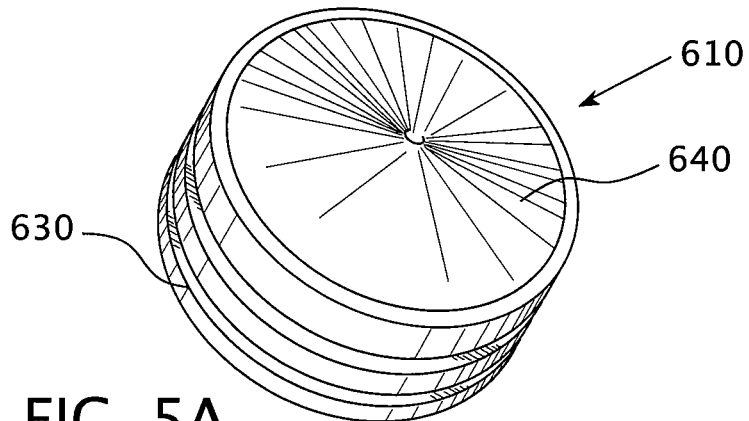
FIG. 5A illustrates a front perspective view of another embodiment of a plunger of the present invention.
Figure 5B:
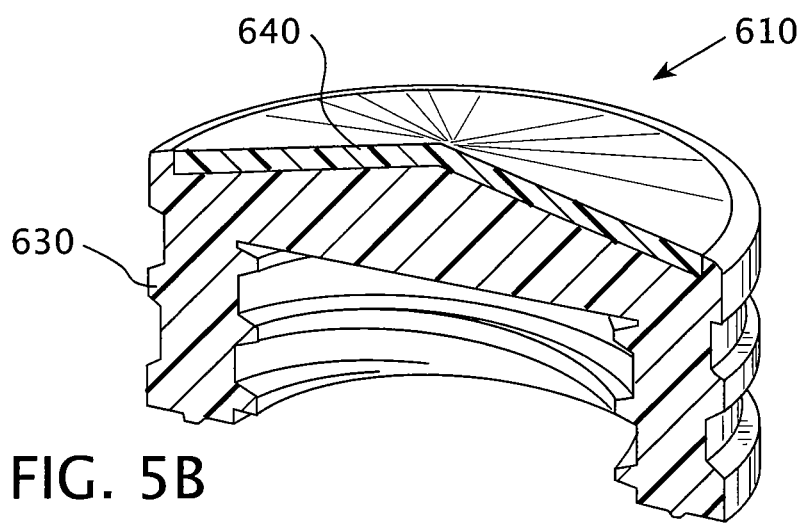
FIG. 5B illustrates a perspective, cutaway view of the plunger of FIG. 5A.
Figure 5C:
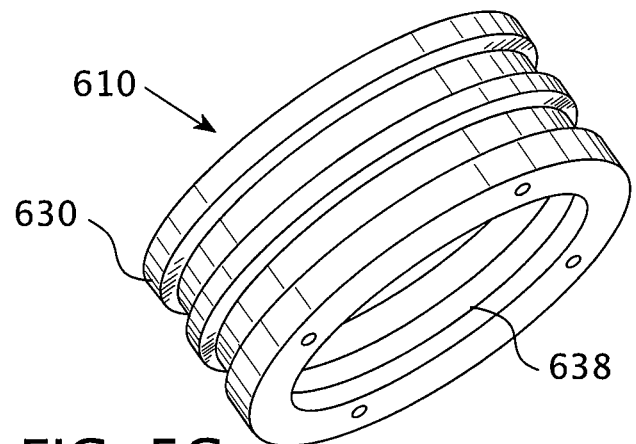
FIG. 5C illustrates a rear perspective view of the plunger of FIG. 5A.
Figure 5D:
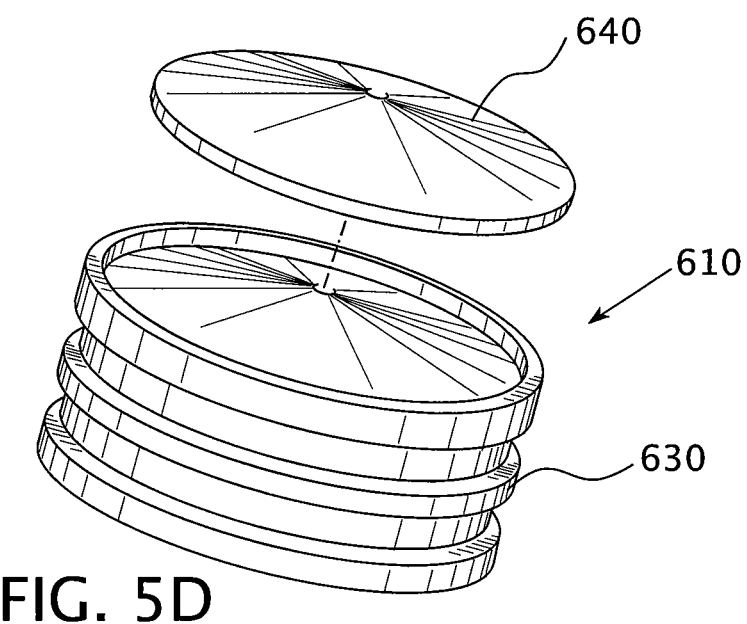
FIG. 5D illustrates a front perspective, exploded view of the plunger of FIG. 5A.
Figure 5E:
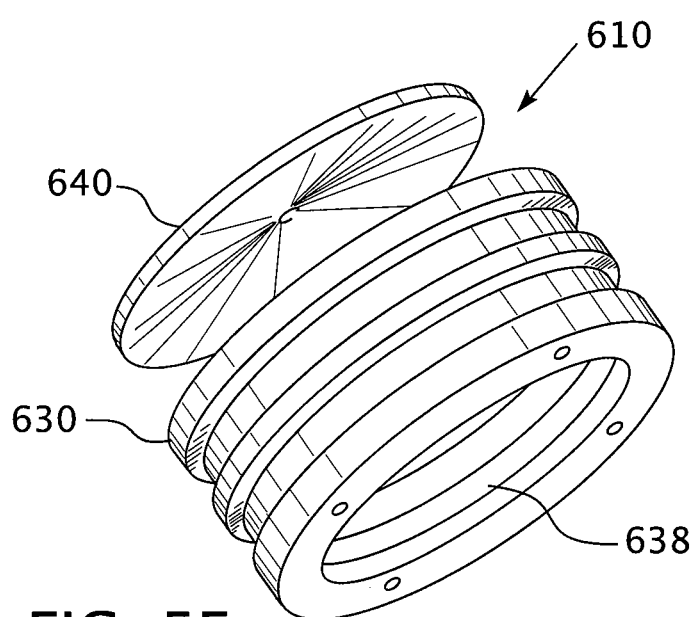
FIG. 5E illustrates a front perspective, exploded view of the plunger of FIG. 5A.

FIGS. 5A through 5E illustrate another embodiment of a plunger 610 of the present invention. Unlike the plunger embodiments set forth above, plunger 610 does not include a plunger base or support as, for example, described in connection with base or support ring 50. In that regard, a sealing portion 630 (formed or molded from and elastomeric material such as a TPE/TPU material) includes a seating 638 (for example, a threaded seating) to form a connection (for example, a removable connection) with a drive member. A rigid central portion 640 can, for example, be connected with sealing portion 630 in an overmolding process as described above.

The foregoing description and accompanying drawings set forth the preferred embodiments of the invention at the present time. Various modifications, additions and alternative designs will, of course, become apparent to those skilled in the art in light of the foregoing teachings without departing from the scope of the invention. The scope of the invention is indicated by the following claims rather than by the foregoing description. All changes and variations that fall within the meaning and range of equivalency of the claims are to be embraced within their scope.

What is claimed is:

1. A plunger cover for use with a syringe, the plunger cover comprising:
    a sealing portion adapted to form a seal with the syringe; and
    a central portion adapted to contact a fluid within the syringe, the central portion being more rigid than the sealing portion, the sealing portion and the central portion being connected in an overmolding process,
    wherein the sealing portion is injection molded first and the central portion is injection overmolded thereon,
    wherein the central portion comprises a conical hollow portion,
    wherein the sealing portion comprises a conical central section,
    wherein the sealing portion and the central portion are overmolded such that the conical central section and the conical hollow portion are coextensively connected to form a multilayer conical portion of the plunger cover, and
    wherein the plunger cover contains colorant.

2. The plunger cover of claim 1, wherein the colorant is contained in the sealing portion, the central portion, or combinations thereof.

3. The plunger cover of claim 1, wherein the sealing portion is formed from a thermoplastic elastomer or a thermoplastic polyurethane.

4. The plunger cover of claim 1, wherein the central portion is formed from polypropylene, acrylonitrile butadiene styrene, or polycarbonate.

5. The plunger cover of claim 1, wherein a material for the sealing portion is a first material and a material for the central portion is a second material, the first material and the second material arc different and are selected so that molecular bonding occurs between the sealing portion and the central portion.

6. The plunger cover of claim 1, wherein the central portion is positioned forward of at least a portion of the sealing portion.

7. The plunger cover of claim 1, wherein the sealing portion is shaped to not contact the fluid within the syringe.

8. The plunger cover of claim 1, wherein the sealing portion comprises an inwardly projecting flange seated in a seating formed in a support ring.

9. A plunger for use with a syringe, the plunger comprising:
    a plunger cover comprising a sealing portion adapted to form a seal with the syringe and a central portion adapted to contact a fluid within the syringe, the central portion being more rigid than the sealing portion, the sealing portion and the central portion being connected in an overmolding process; and a support ring attached to the plunger cover, wherein the support ring has a forward surface shaped to contact and mate with a rearward surface of the plunger cover, wherein the central portion of the plunger cover comprises a conical hollow portion, wherein the sealing portion of the plunger cover comprises a conical central section, wherein the sealing portion and the central portion are overmolded such that the conical central section and the conical hollow portion are coextensively connected to form a multilayer conical portion of the plunger cover, and wherein the plunger contains colorant.

10. The plunger of claim 9, wherein the colorant is contained in the central portion, the sealing portion, the support ring, or combinations thereof.

11. The plunger of claim 9, wherein the sealing portion is formed from a thermoplastic elastomer or a thermoplastic polyurethane.

12. The plunger of claim 9, wherein the central portion is formed from polypropylene, acrylonitrile butadiene styrene or polycarbonate.

13. The plunger of claim 9, wherein a material for the sealing portion is a first material and a material for the central portion is a second material, the first material and the second material are different and are selected so that molecular bonding occurs between the sealing portion and the central portion.

14. The plunger of claim 9, wherein the sealing portion includes a radially inward projecting flange that is seated within a seating formed on the support ring to connect the plunger cover to the support ring.

15. The plunger of claim 9, wherein the forward surface of the support ring abuts the plunger cover to prevent rearward motion of the central portion of the plunger cover relative to the support ring.

16. A syringe comprising:

a syringe body and a plunger slidably positioned within the syringe body, the plunger comprising a plunger cover comprising:

a sealing portion adapted to form a seal with the syringe body;

a central portion adapted to contact a fluid within the syringe, the central portion being more rigid than the sealing portion, the sealing portion and the central portion being connected in an overmolding process; and a support ring attached to the plunger cover, wherein the sealing portion is injection molded first and the central portion is injection molded thereon, wherein the support ring has a forward surface shaped to contact and mate with a rearward surface of the plunger cover, wherein the central portion comprises a conical hollow portion, wherein the sealing portion comprises a conical central section, wherein the sealing portion and the central portion are overmolded such that the conical central section and the conical hollow portion are coextensively connected to form a multilayer conical portion of the plunger cover, and wherein the plunger cover contains colorant.

17. The syringe of claim 16, wherein the colorant is contained in the central portion, the sealing portion, the support ring, or combinations thereof.

* * * * *

UNITED STATES PATENT AND TRADEMARK OFFICE
CERTIFICATE OF CORRECTION

PATENT NO. : 9,855,390 B2  
APPLICATION NO. : 14/576354  
DATED : January 2, 2018  
INVENTOR(S) : Bisegna et al.

Page 1 of 1

It is certified that error appears in the above-identified patent and that said Letters Patent is hereby corrected as shown below:

In the Specification  
In Column 1, Line 8, delete "2007," and insert -- 2007, now Pat. No. 8,926,569, --, therefor.  
In Column 3, Line 27, delete "can." and insert -- can, --, therefor.  
In Column 4, Line 28, delete "FIG. 3A." and insert -- FIG. 4A. --, therefor.  
In Column 5, Line 9, delete "FIG. 1A through 1G," and insert -- FIGS. 1A through 1F, --, therefor.  
In Column 5, Line 52, delete "it's" and insert -- its --, therefor.  
In Column 6, Line 37, delete "100" and insert -- 100. --, therefor.  
In Column 6, Line 65, delete "from" and insert -- form --, therefor.

In the Claims  
In Column 8, Line 53, in Claim 5, delete "arc" and insert -- are --, therefor.  
In Column 8, Line 67, in Claim 9, delete "syringe and" and insert -- syringe; and --, therefor.

Signed and Sealed this  
Third Day of April, 2018

Andrei Iancu  
*Director of the United States Patent and Trademark Office*